United States Patent
Shade et al.

(10) Patent No.: US 12,311,052 B2
(45) Date of Patent: May 27, 2025

(54) MITOCHONDRIAL PERFORMANCE ENHANCEMENT NANOEMULSION METHOD

(71) Applicant: Quicksilver Scientific, Inc., Louisville, CO (US)

(72) Inventors: Christopher W. Shade, Louisville, CO (US); Steven Tieu, Louisville, CO (US)

(73) Assignee: Quicksilver Scientific, Inc., Louisville, CO (US)

( * ) Notice: Subject to any disclaimer, the term of this patent is extended or adjusted under 35 U.S.C. 154(b) by 436 days.

(21) Appl. No.: 17/730,571

(22) Filed: Apr. 27, 2022

(65) Prior Publication Data

US 2022/0304927 A1 Sep. 29, 2022

Related U.S. Application Data

(62) Division of application No. 16/214,289, filed on Dec. 10, 2018, now Pat. No. 11,344,497.

(60) Provisional application No. 62/596,338, filed on Dec. 8, 2017.

(51) Int. Cl.
| | |
|---|---|
| A61K 9/107 | (2006.01) |
| A61K 31/05 | (2006.01) |
| A61K 31/122 | (2006.01) |
| A61K 47/10 | (2017.01) |
| A61K 47/14 | (2017.01) |
| A61K 47/22 | (2006.01) |
| A61K 47/24 | (2006.01) |
| A61K 9/00 | (2006.01) |
| A61K 9/1277 | (2025.01) |
| B82Y 5/00 | (2011.01) |

(52) U.S. Cl.
CPC ............ *A61K 9/1075* (2013.01); *A61K 31/05* (2013.01); *A61K 31/122* (2013.01); *A61K 47/10* (2013.01); *A61K 47/14* (2013.01); *A61K 47/22* (2013.01); *A61K 47/24* (2013.01); *A61K 9/0053* (2013.01); *A61K 9/1277* (2013.01); *B82Y 5/00* (2013.01)

(58) Field of Classification Search
None
See application file for complete search history.

(56) References Cited

U.S. PATENT DOCUMENTS

| | | |
|---|---|---|
| 5,238,683 A | 8/1993 | Crystal |
| 5,260,065 A | 11/1993 | Mathur et al. |
| 5,395,619 A | 3/1995 | Zalipsky et al. |
| 5,565,439 A | 10/1996 | Piazza et al. |
| 5,569,464 A | 10/1996 | Endo et al. |
| 5,711,965 A | 1/1998 | Ghyczy et al. |
| 5,817,695 A | 10/1998 | Pellico |
| 5,834,014 A | 11/1998 | Weiner et al. |
| 5,871,769 A | 2/1999 | Fleming et al. |
| 5,935,588 A | 8/1999 | Afriat et al. |
| 6,048,886 A | 4/2000 | Neigut |
| 6,143,786 A | 11/2000 | Gohman et al. |
| 6,159,500 A | 12/2000 | Demopoulos et al. |
| 6,180,662 B1 | 1/2001 | Lanzendorfer et al. |
| 6,204,248 B1 | 3/2001 | Demopoulos et al. |
| 6,218,436 B1 | 4/2001 | Howard et al. |
| 6,235,271 B1 | 5/2001 | Luther et al. |
| 6,245,797 B1 | 6/2001 | Winokur |
| 6,287,611 B1 | 9/2001 | Morello et al. |
| 6,319,517 B1 | 11/2001 | Cavallo et al. |
| 6,337,065 B1 | 1/2002 | Jacobson et al. |
| 6,358,516 B1 | 3/2002 | Harod |
| 6,492,410 B1 | 12/2002 | Leopold et al. |
| 6,534,540 B2 | 3/2003 | Kindness et al. |
| 6,562,369 B2 | 5/2003 | Luo et al. |
| 6,596,305 B1 | 7/2003 | Edgerly-Plug |
| 6,630,157 B1 | 10/2003 | Horrobin et al. |
| 6,713,533 B1 | 3/2004 | Panzner |
| 6,764,693 B1 | 7/2004 | Smith |
| 7,825,084 B2 | 11/2010 | Harris et al. |
| 8,067,381 B1 | 11/2011 | Harris et al. |
| 8,114,913 B1 | 2/2012 | Guilford et al. |
| 8,147,869 B2 | 4/2012 | Guilford et al. |
| 8,252,325 B2 | 8/2012 | Guilford et al. |
| 8,282,977 B2 | 10/2012 | Bromley |
| 8,349,359 B2 | 1/2013 | Guilford et al. |
| 8,679,530 B2 | 3/2014 | Guilford et al. |
| 8,741,373 B2 | 6/2014 | Bromley et al. |
| 9,474,725 B1 | 10/2016 | Reillo et al. |
| 9,730,911 B2 | 8/2017 | Verzura et al. |
| 9,839,612 B2 | 12/2017 | Reillo et al. |
| 9,925,149 B2 | 3/2018 | Kaufman |
| 9,972,680 B2 | 5/2018 | Reillo et al. |

(Continued)

FOREIGN PATENT DOCUMENTS

| | | |
|---|---|---|
| EP | 0834301 A1 | 4/1998 |
| WO | 199111117 A2 | 8/1992 |

(Continued)

OTHER PUBLICATIONS

Amory, et al., "Oral Testosterone in Oil Plus Dutasteride in Men: A Pharmacokinetic Study", The Journal of Clinical Endocrinology & Metabolism, 90(5), May 2005, 2610-2617.

(Continued)

*Primary Examiner* — Nannette Holloman
(74) *Attorney, Agent, or Firm* — Blanchard Horton PLLC

(57) ABSTRACT

An aqueous, intra-oral, nanoemulsion blend is provided that enhances mitochondrial performance in mammals when orally administered. The blend includes at least two different monolayer surfactant bound particle components and at least one bilayer water-core liposome component. The blend optionally may include a micelle.

18 Claims, 2 Drawing Sheets

(56) References Cited

U.S. PATENT DOCUMENTS

| | | |
|---|---|---|
| 9,974,739 B2 | 5/2018 | Reillo et al. |
| 10,016,389 B2 | 7/2018 | Zhang |
| 10,084,044 B2 | 9/2018 | Reillo et al. |
| 10,103,225 B2 | 10/2018 | Reillo et al. |
| 10,239,808 B1 | 3/2019 | Black et al. |
| 10,722,465 B1 | 7/2020 | Shade et al. |
| 2002/0025313 A1 | 2/2002 | Micklus et al. |
| 2002/0048551 A1 | 4/2002 | Keller et al. |
| 2002/0102316 A1 | 8/2002 | Weissman |
| 2002/0106339 A1 | 8/2002 | Fisher et al. |
| 2002/0132781 A1 | 9/2002 | Kindness et al. |
| 2002/0137785 A1 | 9/2002 | Kindness et al. |
| 2002/0169195 A1 | 11/2002 | Kindness et al. |
| 2002/0182585 A1 | 12/2002 | Kindness et al. |
| 2002/0187130 A1 | 12/2002 | Kindness et al. |
| 2003/0059462 A1 | 3/2003 | Barenholz et al. |
| 2003/0083241 A1 | 5/2003 | Young |
| 2003/0096000 A1 | 5/2003 | Solis et al. |
| 2003/0157220 A1 | 8/2003 | Morello et al. |
| 2003/0162829 A1 | 8/2003 | Kindness et al. |
| 2004/0022841 A1 | 2/2004 | Hassan et al. |
| 2004/0022873 A1 | 2/2004 | Guilford et al. |
| 2004/0127476 A1 | 7/2004 | Kershman et al. |
| 2004/0170560 A1 | 9/2004 | Fossheim et al. |
| 2004/0219123 A1 | 11/2004 | Astruc et al. |
| 2005/0131041 A1 | 6/2005 | Salman et al. |
| 2005/0191343 A1 | 9/2005 | Liang |
| 2006/0099244 A1 | 5/2006 | Guilford |
| 2006/0106093 A1 | 5/2006 | Rich et al. |
| 2007/0065456 A1 | 3/2007 | Woods |
| 2008/0131496 A1 | 6/2008 | Guilford |
| 2008/0207679 A1 | 8/2008 | Berkowitz |
| 2009/0047340 A1 | 2/2009 | Guilford |
| 2009/0068253 A1 | 3/2009 | Guilford |
| 2009/0069279 A1 | 3/2009 | Astruc et al. |
| 2010/0086573 A1 | 4/2010 | Anderson |
| 2010/0166846 A1 | 7/2010 | Guilford |
| 2010/0173882 A1 | 7/2010 | Giliyar et al. |
| 2010/0233193 A1 | 9/2010 | Guilford et al. |
| 2010/0233297 A1 | 9/2010 | Guilford et al. |
| 2010/0291196 A1 | 11/2010 | Guilford |
| 2010/0316700 A1 | 12/2010 | Guilford |
| 2011/0020436 A1 | 1/2011 | Guilford |
| 2011/0129523 A1 | 6/2011 | Guilford et al. |
| 2011/0274625 A1 | 11/2011 | Redelmeier et al. |
| 2011/0305752 A1 | 12/2011 | Guilford et al. |
| 2012/0087994 A1 | 4/2012 | Guilford et al. |
| 2012/0135068 A1 | 5/2012 | Guilford et al. |
| 2012/0141608 A1 | 6/2012 | Guilford et al. |
| 2012/0171280 A1 | 7/2012 | Zhang |
| 2012/0219616 A1 | 8/2012 | Guilford et al. |
| 2012/0282325 A1 | 11/2012 | Tong et al. |
| 2013/0045271 A1 | 2/2013 | Dadey et al. |
| 2013/0084326 A1 | 4/2013 | Howe |
| 2013/0231297 A1 | 9/2013 | Krawitz |
| 2014/0127288 A1 | 5/2014 | Ikemoto |
| 2014/0161784 A1 | 6/2014 | Westerlund et al. |
| 2015/0079156 A1 | 3/2015 | Kett et al. |
| 2015/0157570 A1 | 6/2015 | Babiychuk |
| 2015/0296856 A1 | 10/2015 | Chandra et al. |
| 2016/0166516 A1 | 6/2016 | Gannon et al. |
| 2016/0263047 A1 | 9/2016 | Kaufman |
| 2017/0127712 A1 | 5/2017 | Yiannios |
| 2017/0189447 A1 | 7/2017 | Morris |
| 2018/0263283 A1 | 9/2018 | Popplewell et al. |

FOREIGN PATENT DOCUMENTS

| | | |
|---|---|---|
| WO | 199855075 A2 | 12/1998 |
| WO | 20010126618 A2 | 4/2001 |
| WO | 2008100629 A2 | 8/2008 |
| WO | 2012066334 A1 | 5/2012 |
| WO | 2016020485 A1 | 2/2016 |

OTHER PUBLICATIONS

Casson, et al., "Delivery of Dehydroepiandrosterone to Premenopausal Women: Effects of Micronization and Nonoral Administration", American Journal of Obstetrics and Gynecology, 174(2), Retrieved from :<<http://www.hormonebalance.org/images/documents/Casson%2096%20Vag%20vs%20oral%20DHEA%20AJOG.pdf>>, Feb. 1996, 649-653.

Farina, et al., "Metals, Oxidative Stress and Neurodegeneration: A Focus on Iron, Manganese and Mercury", NIH Public Access, Neurochem Int., 62(5), Apr. 2013, 575-594.

Hazekamp, Arno, "The Trouble with CBD Oil", Medical Cannabis & Cannabinoids, 1, Jun. 12, 2018, 65-72.

Kale, et al., "Emulsion Micro Emulsion and Nano Emulsion: A Review", Sys Rev Pharm, 8(1), 2017, 39-47.

Tan, et al., "Tocotrienols Vitamin E Beyond Tocopherols", CRC Press, Second Edition, Sec. 2.3, Nov. 16, 2016, 2 Pages.

MITOCHONDRIAL PERFORMANCE ENHANCEMENT NANOEMULSION METHOD

REFERENCE TO RELATED APPLICATIONS

This application is a division of U.S. Nonprovisional application Ser. No. 16/214,289, filed Dec. 10, 2018, entitled "Mitochondrial Performance Enhancement Nanoemulsion," which claims the benefit of U.S. Provisional Application No. 62/596,338 entitled "Compositions & Methods for Enhancing Mitochondrial Performance" filed Dec. 8, 2017, both of which are incorporated by reference in the entirety.

BACKGROUND

Negative health and disease states are associated with low mitochondrial cellular content and mitochondria damage in the cells of mammals. Such negative health and disease states include cardiomyopathy, lactic acidosis, developmental delay, failure to thrive, impaired neurological function, and obesity. The obesity link is believed attributable to many of the genes that encode for mitochondrial proteins being inversely correlated with body mass.

Pyrroloquinoline quinone disodium salt (PQQ), resveratrol, genistein, hydroxytyrosol, and quercetin are reported to stimulate mitochondrial biogenesis (the formation of new mitochondria) and to improve mitochondrial respiratory control. Resveratrol and genistein are believed to affect cell-signaling pathways important for mitochondrial biogenesis, but lack the water solubility of PQQ. PQQ is believed to protect brain, other nerve, and heart tissue against damage from oxygen radicals and is known to increase growth in animal cells, bacteria, and plants.

PQQ is naturally found in kiwifruit and human breast milk at pico- to nano-molar concentrations. As an ingested solid, it is proposed that milligram quantities of PQQ are needed per kilogram of diet to provide enhanced mitochondrial biogenesis. Micromolar concentrations of PQQ per kilogram of diet are believed necessary to provide enhanced mitochondrial biogenesis when PQQ is injected. Unlike Vitamin C, PQQ can undergo thousands of redox cycles without degradation or polymerization. PQQ is also somewhat unique in that it can be detected in tissue with little or no dietary exposure.

Prior studies have demonstrated that mice and rats fed diets lacking PQQ have reduced mitochondrial content. Conversely, Hepa1-6 mouse cells exposed to 10-30 μM PQQ for 24-48 hours demonstrated increased citrate synthase and cytochrome c oxidase activity, Mitotracker staining, mitochondrial DNA content, and cellular oxygen respiration. PQQ also was shown to protect cells from mitochondrial inhibition by rotenone, 3-nitropropionic acid, antimycin A, and sodium azide. *J. Biol. Chem.*, Jan. 1, 2010; 285(1): 142-152.

In animals, dietary PQQ deprivation results in abnormal development, immune dysfunction, and decreased reproductive performance. While PQQ is believed to affect many genes, the most affected genes are believed those involved in mitochondrial-related function. For example, in a mouse example, PQQ deficient mice have a 20 to 30% reduction in the relative amount of mitochondria in the liver when compared to PQQ supplemented mice.

Resveratrol (3,5,4'-trihydroxy-trans-stilbene) is produced by several plants in response to injury or, when the plant is under attack by pathogens, such as bacteria or fungi. Sources of resveratrol in food include the skin of grapes, blueberries, raspberries, and mulberries. Resveratrol exists as two geometric isomers: cis-(Z) and trans-(E). The trans- and cis-resveratrol isomers can be either free or bound to glucose. While 70% of orally administered resveratrol is absorbed by the body, the bioavailability is only about 0.5% as resveratrol is extensively metabolized into its glucuronide conjugate by the liver and intestine before reaching the bloodstream. In animal models, it is believed that from 200 to 500 milligrams (mg) of resveratrol is needed per kilogram of diet to enhance mitochondrial biogenesis.

Coenzyme Q10 (CoQ10) is present in animals and most bacteria. CoQ10 is considered to have structural similarity to a vitamin and is present in all respiring eukaryotic cells, primarily in the mitochondria. It is a component of the mitochondrial electron transport chain and participates in aerobic cellular respiration, which generates energy in the form of ATP. Therefore, those organs with the highest energy requirements—such as the heart, liver, and kidney—have the highest CoQ10 concentrations as they have the highest concentration of mitochondria. Having three redox states, CoQ10 can act as a two or one electron carrier in the mitochondrial electron transport chain. Thus, CoQ10 can provide a single electron, as needed for electron transport to iron-sulfur clusters, and can also function to scavenge (deactivate) free radicals, such as oxygen radicals. While readily measured in blood plasma, this is an indication of dietary CoQ10 intake, not tissue concentration. The body can produce CoQ10 similarly to cholesterol, but CoQ10 synthesis may be inhibited by some beta-blockers, blood-pressure reduction medication, and severely limited by statins. When consumed orally, CoQ10 has an approximate 10% bioavailability.

Vitamin E includes the tocotrienols (alpha, beta, gamma, and delta isomers) and the tocopherols (alpha, beta, gamma, and delta isomers), which are all oil-soluble. All tocotrienol and tocopherol isomers (thus, all forms of Vitamin E) have some antioxidant activity due to an ability to donate a hydrogen atom (a proton plus electron) to an oxygen radical—thus deactivating the radical by forming an —OH (alcohol) group. The critical chemical structural difference between the tocotrienol and tocopherol forms of Vitamin E is that the tocopherols have saturated side chains, while the tocotrienols have unsaturated isoprenoid side chains with three double bonds. The different tocotrienol isomers demonstrate different bioavailability and efficacy depending on the type of antioxidant performance being measured. Conventionally, alpha-tocopherol has been the preferred form of "Vitamin E", as this oil-soluble tocopherol isomer is credited with having the highest antioxidant biological activity and is preferentially absorbed and accumulated in humans when orally consumed.

Adaptogens or adaptogenic substances describe compounds that when administered to a living organism decrease cellular sensitivity to stress. While adaptogens may have multiple pathways of action, a primary role of an adaptogen is to reduce the cortisol response, thus the body's production of cortisol in response to stress. Humans produce cortisol in response to stress and/or low blood sugar. Cortisol will increase blood sugar through increased metabolism of fat, protein, and carbohydrate, while simultaneously suppressing the immune system and bone growth.

The effect of cortisol on the immune system is substantial, as evidenced by the hydrocortisone form of cortisol being used as a medication to reduce unwanted immune response, such as skin inflammation and rash. Elevated levels of cortisol arising from the stress response have known deleterious effects on the immune system. For example, wounds from punch biopsies of students took an average of 40% longer to heal when performed three days before an examination as opposed to biopsies performed on the same students during summer vacation.

FIG. 1A and FIG. 1B represent a liposome 100 having a double wall (bilayer) of phospholipids formed from a hydrophilic exterior wall 120 and a hydrophilic interior wall 125. The interior of the double wall 110 is hydrophobic. The hydrophilic interior wall 125 forms a capsule interior 130, to form what may be referred to as a "water-core" liposome. Liposomes may be thought of as small, fluid-filled capsules where the wall of the capsule is formed from two layers of a phospholipid. As phospholipids make up the outer membranes of living cells, the liposome 100 can be thought of as having an outer, permeable membrane wall like a cell, but without a nucleus or the other components of a living cell within the capsule interior 130. The outer and inner walls 120, 125 of the represented liposome 100 are water-soluble, while the interior of the wall 125 is fat-soluble. A common phospholipid used to form liposomes is phosphatidylcholine (PC), a material found in lecithin.

When introduced to the body, liposomes are known to deliver their internal contents to living cells through one of four methods: adsorption, endocytosis, lipid exchange, and fusion. In adsorption, the outer wall of the liposome sticks to the living cell and releases its contents through the outer wall of the living cell into the living cell. In endocytosis, the living cell consumes the liposome, thus bringing the entire liposome into the cell. The cell then dissolves the outer wall of the liposome and releases the liposome contents into the interior of the living cell. In lipid exchange, the liposome opens in close proximity to the living cell and the living cell takes in the localized high concentration of liposome interior. In fusion, the outer wall of the liposome becomes part of the outer wall of the living cell, thus carrying the contents of the liposome into the enlarged living cell. These pathways allow for a potential 100% transfer of the interior contents of the liposome to the interior of the living cell, if the liposome can be brought into close proximity to the cell and is properly constructed to interact with the target cell.

FIG. 2 represents a flattened side view of the double wall (bilayer) of phospholipids that forms the liposome. The phospholipids have polar, hydrophilic "heads" and less polar, relatively hydrophobic "tails". In this representation, the heads form the top and bottom of the bilayer, with the tails forming the interior middle. Oil-soluble compounds can reside between the top and bottom layers within the interior area occupied by the tails.

FIG. 3 represents a micelle 300 having a single wall of phospholipids (monolayer) forming a hydrophilic exterior 320 and a hydrophobic interior 310 lacking the hydrophilic capsule interior of a liposome. Thus, in relation to a liposome, a micelle lacks a bilayer and does not provide the capsule interior that can contain a water-soluble, hydrophilic core composition. The micelle 300 may be thought of as the outer wall of a liposome without the inner wall providing for a capsule interior. Polyethylene glycol modified vitamin E, such as tocopheryl polyethylene glycol succinate 1000 (TPGS), may be used to form micelles in water as the TPGS has a water-soluble head and an oil-soluble tail.

FIG. 4 represents a monolayer surfactant where the oil component is associated with the hydrophobic tails of a surfactant. In this representation, the surfactant has formed a circular shape, thus encircling the oil component and approximating a relatively large, expanded micelle, but that is not required for the oil component to associate with the hydrophobic tails.

Nutritional supplements are conventionally introduced to the bloodstream in multiple ways. Supplements taken orally are adsorbed at different rates due to many factors. For example, on average about 10% to 20% of a solid supplement taken orally is adsorbed. This can be increased to about 30% with an orally taken gel capsule, to about 45% with a transdermal patch, and to about 50% with a conventional intra-oral (sublingual). Injections provide from approximately 90% to 100% adsorption, but are uncommonly used for nutritional supplements.

The present invention avoids or ameliorates at least some of the disadvantages of conventional oral supplement preparations intended to enhance mitochondrial performance in a living organism.

SUMMARY

In one aspect, the invention provides an aqueous, intra-oral, nanoemulsion blend for enhancing mitochondrial performance in animals when orally administered, the blend includes at least two different monolayer surfactant bound particle components, where a first particle component includes at least one amphiphilic fat, a polyethylene glycol surfactant form, an associating oil, and a cell-signaling pathway enhancement composition, and a second particle component includes at least one amphiphilic fat, a polyethylene glycol surfactant form, an associating oil, and coenzyme Q10; and at least one bilayer water-core liposome particle component, where the at least one bilayer water-core liposome particle component includes at least one amphiphilic fat forming a capsule interior, where the capsule interior includes a pyrroloquinoline quinone salt dissolved in water In another aspect of the invention, there is an aqueous, intra-oral, nanoemulsion blend for enhancing mitochondrial performance in animals when orally administered, the blend including at least two different monolayer surfactant bound particle components, where a first particle component comprises at least one amphiphilic fat, a polyethylene glycol surfactant form, an associating oil, and a cell-signaling pathway enhancement composition, and a second particle component comprises at least one amphiphilic fat, a polyethylene glycol surfactant form, an associating oil, and coenzyme Q10; and at least one bilayer water-core liposome component, where the at least one bilayer water-core liposome component includes at least one amphiphilic fat forming a capsule interior, where the capsule interior includes an adaptogenic herb extract in water, the adaptogenic herb extract including water- and oil-soluble adaptogenic herbs.

In another aspect of the invention, there is an aqueous, intra-oral, nanoemulsion blend for enhancing mitochondrial performance in an animal when orally administered, the blend including a cell-signaling pathway enhancement composition delivery means for delivering a cell-signaling pathway enhancement composition to the bloodstream of the animal; a coenzyme Q10 delivery means for delivering coenzyme Q10 to the bloodstream of the animal; and a pyrroloquinoline quinone salt delivery means for delivering a pyrroloquinoline quinone salt to the bloodstream of the animal, where when administered intra-orally to an animal the cell-signaling pathway enhancement composition delivery means, the coenzyme Q10 delivery means, and the pyrroloquinoline quinone salt delivery means in combination are configured to provide a total bloodstream delivered concentration ratio for the pyrroloquinoline quinone salt to the cell-signaling pathway enhancement composition from 1:1 to 1:2 and for the pyrroloquinoline quinone disodium salt to the coenzyme Q10 from 1:2 to 1:4.

In another aspect of the invention, there is a method of making an aqueous, intra-oral, nanoemulsion blend for enhancing mitochondrial performance in animals when orally administered, the method includes homogenizing a mixture comprising a cell-signaling pathway enhancement composition, a first portion of amphiphilic fat including at least 30% by weight phosphatidylcholine, a polyethylene glycol surfactant form, an associating oil, glycerin, ethanol, and water to form a first emulsion; homogenizing a mixture comprising coenzyme Q10, a second portion of amphiphilic fat including at least 30% by weight phosphatidylcholine, a polyethylene glycol surfactant form, an associating oil, glycerin, ethanol, and water to form a second emulsion; combining the first and second emulsions with at least one tocotrienol isomer of Vitamin E to form a third emulsion; combining a third portion of amphiphilic fat including at least 30% by weight phosphatidylcholine with glycerin and ethanol in water to form micellular amphiphilic fat; combining an adaptogenic herb extract including oil- and water-soluble herbs, water, ethanol, and glycerin with a fourth portion of amphiphilic fat including at least 30% by weight phosphatidylcholine, a polyethylene glycol surfactant form, additional ethanol, and acacia gum in water to form an adaptogenic herb liposome mixture; combining the third emulsion with the micellular amphiphilic fat and the adaptogenic herb liposome mixture to form a fourth emulsion; combining a pyrroloquinoline quinone salt dissolved in water and sodium hydroxide with the fourth emulsion to form a fifth emulsion; and homogenizing the fifth emulsion under a pressure from 100 to 1000 bar to form an aqueous, intra-oral, nanoemulsion blend including phosphatidylcholine micelles.

Other systems, methods, features and advantages of the invention will be, or will become, apparent to one with skill in the art upon examination of the following figures and detailed description. It is intended that all such additional systems, methods, features, and advantages be included within this description, be within the scope of the invention, and be protected by the claims that follow. The scope of the present invention is defined solely by the appended claims and is not affected by the statements within this summary.

BRIEF DESCRIPTION OF THE FIGURES

The invention can be better understood with reference to the following drawings and description. The components in the figures are not necessarily to scale and are not intended to accurately represent molecules, emphasis instead being placed upon illustrating the principles of the invention.

DETAILED DESCRIPTION

Figure 1A:
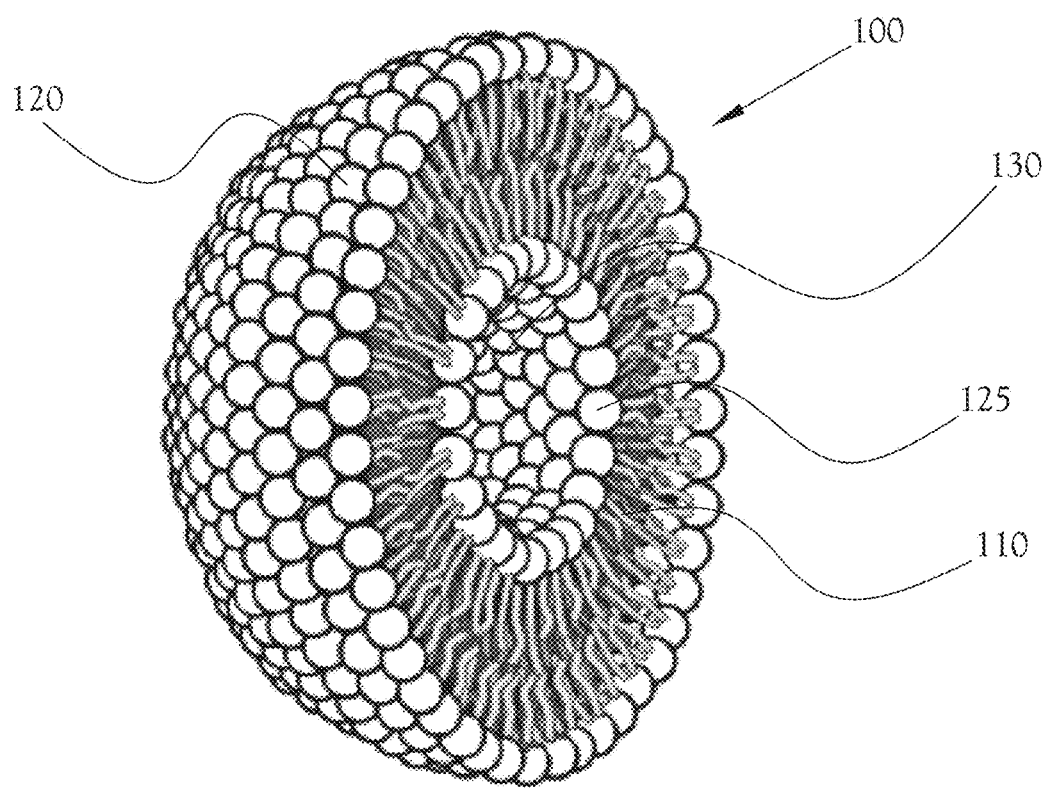
FIG. 1A and FIG. 1B represent a liposome having a double wall of phospholipids forming a hydrophilic exterior and capsule interior with a hydrophobic wall interior.
Figure 1B:
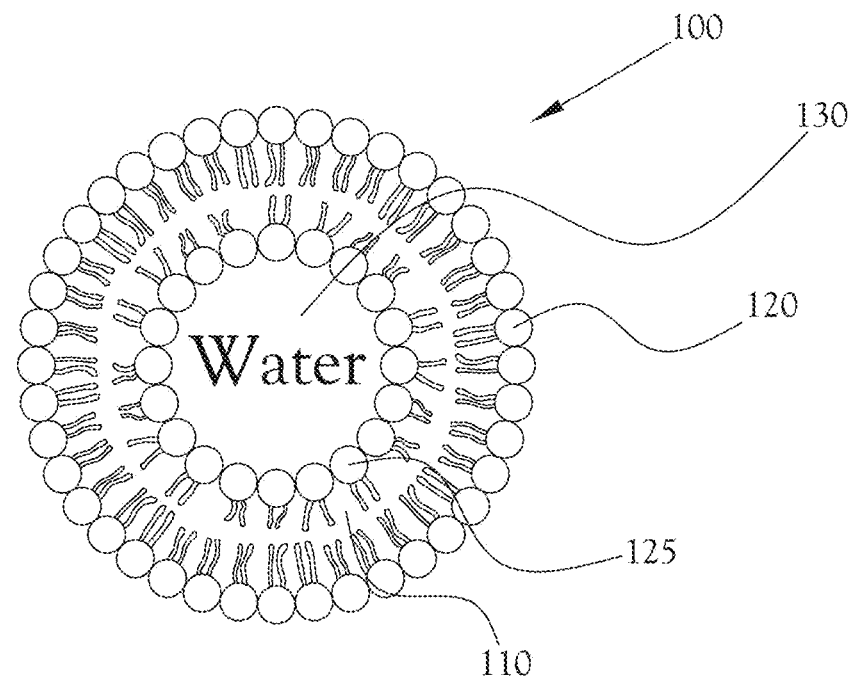
Figure 2:
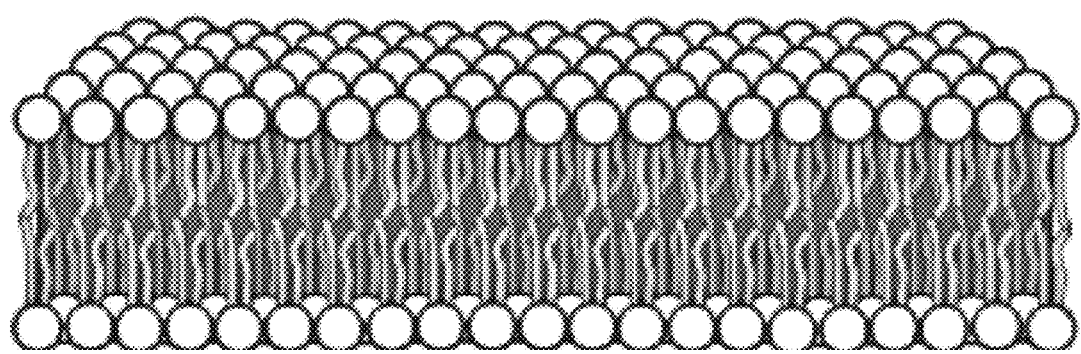
FIG. 2 represents a flattened side view of the double wall (bilayer) of phospholipids that forms the liposome.
Figure 3:
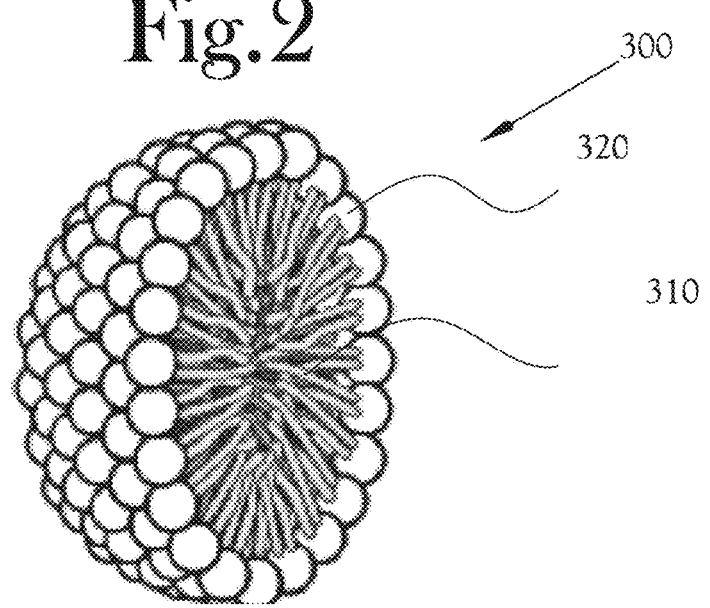
FIG. 3 represents a micelle having a single wall of phospholipids (monolayer) forming a hydrophilic exterior and a hydrophobic interior lacking the capsule interior of a liposome.
Figure 4:
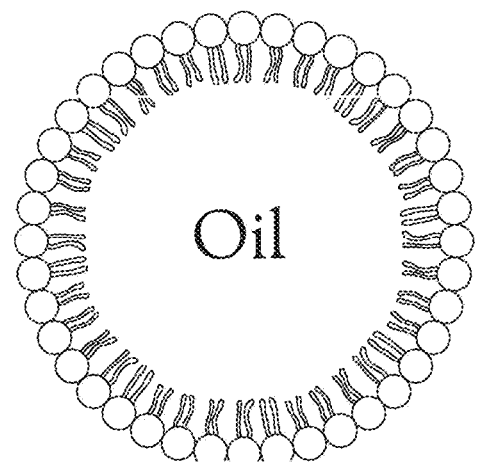
FIG. 4 represents a monolayer surfactant where the oil component is associated with the hydrophobic tails of the surfactant.

An aqueous, intra-oral, nanoemulsion blend is provided that enhances mitochondrial performance in mammals when orally administered. The blend includes at least two different monolayer surfactant bound particle components and at least one bilayer water-core liposome particle component. The blend optionally may include a micelle.

The at least two different monolayer surfactant bound particle components are oil-in-water dispersions where the oil component of the particle is associated with the surfactant system. The oil component of the particle includes oil-soluble components combined with an associating oil that assists in associating the oil-soluble components of the nanoemulsion blend with the surfactant system. The associating oil is selected from the group consisting essentially of medium chain triglycerides (MCT), citrus oil, and combinations thereof.

For the first monolayer surfactant bound particles of the nanoemulsion blend, the oil component is associated with a phosphatidylcholine (PC) and tocopheryl polyethylene glycol succinate (TPGS) surfactant system. The oil component of the first monolayer surfactant bound particles includes a cell-signaling pathway enhancement composition in the associating oil to assist in associating the cell-signaling pathway enhancement composition with the surfactant system. The cell-signaling pathway enhancement composition is preferably resveratrol or genistein, more preferably resveratrol.

For the second monolayer surfactant bound particles of the nanoemulsion blend, the oil component also is associated with a PC and TPGS surfactant system. The oil component of the second monolayer surfactant bound particles includes CoQ10 in the associating oil to assist in associating an electron transport enhancement composition with the surfactant system. An oil-soluble tocotrienol also may be associated with the particles of either or both monolayer surfactant bound particles. The monolayer surfactant bound particles of the nanoemulsion blend are held in a continuous phase.

The third component of the nanoemulsion blend is a bilayer liposome originating from adaptogenic herbs or from PC. If the nanoemulsion blend includes the optional micelle, the micelle is primarily formed from PC. Being water-soluble, PQQ may be carried in the continuous water phase, associated with the hydrophilic heads of the PC, or preferably carried in the interior capsule of a liposome. While formally "water-soluble" the PQQ has a greater affinity for the polar heads of the PC molecules than water, when combined in water. When the PQQ is carried in the interior capsule of a liposome, the liposome is formed primarily from PC. As discussed further below, the nanoemulsion blend allows the PQQ, resveratrol, CoQ10, and optional tocotrienol to be transported to the cells substantially simultaneously and in the desired ratios to maximize the enhancement of mitochondrial performance.

Whether the particles of the nanoemulsion blend are monolayer surfactant bound particles or bilayer water-core liposomes, the particles have an average diameter from 10 to 125 nanometers (nm), preferably from 10 to 80 nm, and more preferably from 10 to 60 nm. The approximately 125-nm average diameter upper limit is important, as particles larger than this will not transport through the tissues of the mouth, but instead will enter the stomach and be substantially irreversibly chemically altered, and thus deactivated, by acid and bile salts.

Intra-oral delivery of the liposomes in combination with the monolayer surfactant bound particles enables rapid, and substantially simultaneous intra-oral adsorption of both the water-soluble constituents and of the oil-soluble constituents of the nanoemulsion blend into the bloodstream. Thus, intra-oral delivery of the nanoemulsion blend in combination with the liposome and monolayer surfactant bound particle structures in the continuous phase prevents the extensive metabolism of the supplement constituents of the nanoemulsion blend observed for conventional, orally-administered supplements.

As the constituents of the nanoemulsion blend are transferred intra-orally to the bloodstream without passing through the gut, substantially enhanced bioavailability is achieved. In fact, the liposomes and accompanying monolayer surfactant bound particles of the nanoemulsion blend can approach IV administration in the rate and concentrations at which the body transfers the supplement constituents of the nanoemulsion blend into the bloodstream. As the nanoemulsion blend substantially avoids digestion by the stomach, liver and intestine, the delivered supplement constituents enter the bloodstream substantially unaltered. In addition to the advantages of not requiring venipuncture for relatively rapid and high bloodstream concentration bioavailability, especially in comparison to conventional oral administration techniques, the nanoemulsion blend may maintain a longer-duration increased concentration of the delivered supplement constituents in the bloodstream than available from an IV injection, and thus a longer duration, high-concentration availability to the living cells.

In addition to water, the aqueous, intra-oral, nanoemulsion blend may include other components including, but not limited to, glycerin, ethanol, sodium hydroxide (NaOH), and a desired flavoring. These other components are selected to not interfere with the beneficial operation of the mitochondrial performance enhancing components or the physical structure of the nanoemulsion blend.

Mitochondrial performance, thus the production efficiency of ATP from glucose and fatty acids within a mammal may be adversely affected by toxins and aging. The toxins may damage the membranes forming the physical structures of the mitochondria or interfere with the electron transport reactions used by the mitochondria to convert fatty acids, glucose, and similar substrates to ATP.

ATP production efficiency also may be adversely affected by age related declines in mitochondrial performance, which generally relate to weakness or deformation of the membranes making up the physical structures forming the mitochondria, or a reduction in the ability of the mitochondria to produce the necessary enzymes and other agents necessary for electron transport. Ninety-five percent of the human body's energy is generated through the aerobic conversion (oxidation) of glucose and fatty acids to ATP within the mitochondria of the cells.

An enhancement of mitochondrial performance per unit time within the cells of a mammal is believed to provide an increase in the health of tissues and organs, in addition to providing enhanced energy, vigor, infection resistance, and weight loss to the mammal. From a tissue/organ perspective, the heart, cardiovascular system, brain, central nervous system (CNS), muscular, and adrenal systems are believed the primary beneficiaries. Much of the health benefits provided by an enhancement in cellular mitochondrial performance is believed attributable to the situation where if enough ATP is not present at a given time, the living cells are forced to ration the available ATP between living, detoxifying, rebuilding their structure, and defending against infection. As cells will primarily chose to live, rationed ATP will result in a retardation in detoxifying, rebuilding, and defending against infection.

The enhancement of mitochondrial performance within the cells of a mammal is believed attainable through one or more of three different pathways. The first pathway is the stimulation of mitochondrial biogenesis (enhanced creation rate of new mitochondria). An enhanced creation rate of new mitochondria is believed to provide an enhancement in mitochondrial performance through an increased longevity of the cell in which the mitochondria reside and an increased rate of energy utilization by the cell—thus an increase in base metabolic rate (BMR). In short, the greater the number of mitochondria in the body, the greater the body's ability to generate ATP per unit time and the more calories that will be consumed per unit time at the same level of musculature and physical activity. From an organ perspective, it is believed that the brain and the heart are the greatest beneficiaries from mitochondrial biogenesis.

The second pathway to enhanced mitochondrial performance may arise from enhancing electron transport within the existing mitochondria, thus accelerating the formation of ATP. The greater the electron transport per unit time within a mitochondria, the greater the amount of ATP that will be available to the living cells, and the less likely destructive rationing will occur.

The third pathway to enhanced mitochondrial performance is believed attainable through the protection of existing mitochondria from radicals, especially when the radicals arise from toxin and heavy metal catalyzed radical formation. Protecting the existing mitochondria in this way is believed to increase the activity and lifespan of the existing mitochondria within the host cell. ATP per unit time generation is believed enhanced through an increase in existing mitochondrial activity by reducing radical damage to the membrane structures of the existing mitochondria. The longer the lifespan of the existing mitochondria within a cell, the greater the total number of mitochondria that will exist within the cell as new mitochondria are produced through biogenesis—thus increasing the body's ability to generate ATP per unit time, as previously discussed.

Enhancing the production of mitochondria within cells (mitochondrial biogenesis) may be accomplished by switching on the genes that produce mitochondria. Peroxisome proliferator-activated receptor-gamma coactivator (PGC1a) is believed to enhance the activity of (trigger) the genes that produce mitochondria. Thus, delivering more bioavailable and bioactive PGC1a to the cells of the body is believed to turn on the systems that produce mitochondria.

The combined delivery of PQQ and resveratrol to the cells by the nanoemulsion is attributed with an increase in PGC1a activity. In the mitochondria, the combination of the PQQ to enhance gene triggering with the cell-signaling pathway enhancement provided by the resveratrol are believed to provide increased mitochondrial biogenesis in relation to either component in isolation. The lack of the combination of the different functions provided by the PQQ and the resveratrol being substantially simultaneously delivered to the cells is believed to explain some of the inconsistent results observed in the literature for these compounds in isolation. PQQ also may be combined with other cell-signaling pathway enhancers, such as genistein.

However, as PQQ is water-soluble, and resveratrol is oil-soluble, they cannot both be delivered to a cell without a carrier system that can transport both water and oil-soluble constituents. In addition to the combination of the hydrophilic PQQ with the hydrophobic cell-signaling pathway enhancer, the ratio of these compounds also is believed important to achieving the desired mitochondrial biogenesis enhancement. Preferably, the ratio of PQQ to resveratrol is from 1:1 to 1:2, preferably from 1:1.2 to 1:1.8, and more preferably from 1:1.4 to 1:1.6. All ratios are given in terms of weight. To achieve these desired ratios at the cellular level, the transport of the PQQ and the resveratrol must be controlled from introduction to the body until both compounds reach the interior of the cells. Otherwise, the body will alter the ratios inconsistently with each introduction as the constituents pass through the gut. Preferably, from 3 to 20 mg of PQQ is included in the nanoemulsion blend; however, the different constituents can be different weights in view of the provided ratios.

Enhancing electron transport within the mitochondria may be accomplished by the coenzyme Q10 (CoQ10). Unless modified, CoQ10 is oil-soluble. While the literature discusses at length the antioxidant properties of this enzyme, we do not believe that the antioxidant properties of the enzyme is the primary function regarding enhancement of mitochondrial performance.

Oxidative phosphorylation (OXPHOS) is the metabolic pathway in which cells use enzymes to oxidize nutrients, thereby releasing energy which is used to form ATP. During OXPHOS, electrons are transferred from electron donors to electron acceptors, such as oxygen, in redox reactions. These redox reactions release energy, which is used to form ATP. In the eukaryote cells of mammals, these redox reactions are carried out by a linked set of protein complexes within the inner membrane of the cell's mitochondria. The linked sets of proteins are called electron transport chains. The energy released by electrons flowing through the electron transport chains is used to transport protons across the inner mitochondrial membrane, in a process called electron transport. This generates potential energy in the form of a pH gradient and an electrical potential across this inner mitochondrial membrane. The store of potential energy within the mitochondria is used by allowing protons to flow back across the inner mitochondrial membrane and down this gradient, through the ATP synthase enzyme. ATP synthase converts the potential energy into ATP. The oxidation of fatty acids within the mitochondria may be thought of as mediated combustion, where the mitochondria reach temperatures of approximately 50° C. (122° F.).

We believe that CoQ10 operates within the mitochondria to increase the rate of electron transport within the interior of the mitochondria. By increasing the availability of CoQ10 within the cell and thus availability to the mitochondria, the rate at which ATP is formed is believed to increase. Preferably, the ratio of PQQ to CoQ10 reaching the cells is from 1:2 to 1:4, preferably from 1:2.4 to 1:3.6, and more preferably from 1:2.8 to 1:3.2. To achieve these desired ratios at the cellular level, the transport of the PQQ and the CoQ10 must be controlled from introduction to the body until both compounds reach the interior of the cells. Without the nanoemulsion blend, the body will alter the ratio of PQQ to CoQ10 inconsistently with each introduction as the constituents pass through the gut.

Protecting the existing mitochondria from oxygen radical damage may be accomplished with a tocotrienol isomer and with the combination of PQQ and the tocotrienol isomer delivered to the cells by the nanoemulsion blend. While the CoQ10 may have some radical inactivation function, as previously discussed, the tocotrienol and the combination of PQQ with the tocotrienol are believed the primary providers of radical protection provided to the mitochondria by the nanoemulsion blend.

Unlike the tocopherol forms of Vitamin E, the tocotrienols are believed to demonstrate superior anticancer, immunomodulatory, and neuroprotective properties. The tocotrienol isomers also are believed to target apoptotic regulators, enzymes, and transcription and growth factors more effectively. While some beneficial effect may be possible regarding mitochondria protection with the tocopherol forms of Vitamin E, we believe the traits of the tocotrienol isomers to be important to the enhancement of mitochondrial performance. The delta isomer of tocotrienol is preferred regarding the enhancement of mitochondrial performance. Presently, we believe it more likely that the tocopherol forms of Vitamin E have a more negative effect on the enhancement of mitochondrial performance than a benefit.

Although OXPHOS is required for a cell to live, the reaction produces reactive oxygen species, such as superoxide and hydrogen peroxide, which lead to the formation of potentially membrane-damaging oxygen radicals. If not sufficiently controlled, the oxygen radicals can damage the membrane structures of the mitochondria, thus contributing to the incidence of disease, and possibly aging, as previously discussed.

The membranes and enzymes of the mitochondria have excellent natural protection against free radical attack when the free radicals are oxygen based—thus, the free radicals that naturally occur within the mitochondria during ATP production. While this protection could be improved, it is inherently very good. For example, if CoQ10 is used to increase electron transport within the mitochondria, an additional source of radical deactivation may be helpful to supplement the natural protection.

In contrast to oxygen-based free radicals, the membranes and enzymes of the mitochondria have poor natural protection to electrophilic toxins and to other toxin structures that form radicals, as the radical protection system inherent to the mitochondria are not conditioned to protect against electrophilic toxins and toxin-based radicals. While many compounds can form electrophiles in the body, for the mitochondria, electrophilic toxins originating from heavy metals, mold toxins, and endotoxins are of primary consideration. Once electrophilic toxins are present within the mitochondria, they can take electrons from the OXPHOS reaction and form radicals within the mitochondria that the natural free radical protection systems inherent within the mitochondria have difficulty inactivating. Such electrophilic toxin originated radicals also may be longer lived than the oxygen radicals normally occurring within the mitochondria due to the molecular structure of the electrophilic toxin or because the mitochondria do not inherently have a system to inactivate the electrophilic toxin radicals. Mold based electrophilic toxin radicals are also believed to damage the mitochondria's inherent oxygen radical defense system, and thus increase the damage caused by the normally formed oxygen radicals.

The tocotrienol isomers of Vitamin E are believed to more readily inactivate electrophilic toxin based free radicals than the tocopherol forms of Vitamin E. Thus, in addition to inactivating oxygen and electrophilic toxin-based radicals, the tocotrienols are believed to better protect the inherent oxygen radical protection system of the mitochondria and preserve its function against oxygen radicals. Preferred tocotrienols for the enhancement of mitochondrial performance are the gamma and delta tocotrienols. The ratio of PQQ to tocotrienol is from 1:0.1 to 1:2, preferably from 1:0.2 to 1:1, and more preferably from 1:0.3 to 1:0.8. To achieve these desired ratios at the cellular level, the transport of the PQQ and the tocotrienol are controlled from introduction to the body until both compounds reach the interior of the cells. Without the nanoemulsion blend, the body will alter the ratio of PQQ to tocotrienol inconsistently with each introduction as the constituents pass through the gut.

In addition to the described direct action of the tocotrienols in relation to toxin-based radicals, the PQQ and the combination of the water-soluble PQQ with the water-soluble tocotrienol is believed to stimulate Nrf2, a nuclear transcription factor. Nrf2 can activate the genes that increase the production of antioxidants by the cells and that increase the production of radical control enzymes. Thus, Nrf2 can increase the capacity of the natural oxygen radical protection system inherent to the mitochondria. The more common tocopherol forms of Vitamin E are believed to inhibit Nrf2.

The nanoemulsion blend preferably also includes water- and oil-soluble adaptogenic herbs. The adaptogenic herbs are provided in water including liposomes. While not believed to act directly on the mitochondria, the ability of these herbs to reduce the cortisol response is believed to provide an added health benefit and to assist in stabilizing the nanoemulsion blend. The adaptogenic herbs preferably included in the nanoemulsion blend include at least three of the following: Acai; Gynostemma (aerial parts) (Jiaogulan); Lycium (fruit) (Himalayan Goji); Maca (root); American Ginseng (root); Siberian Ginseng (root); Schisandra (fruit); Chinese Licorice (root); Rhodiola (root); Astragalus (root); Reishi (fruiting body); Catuaba (bark); Stinging Nettle (aerial parts); Saw Palmetto (fruit); Guarana (seed); Ashwagandha (root); Tribulus (aerial parts); Epimedium (aerial parts); and Yohimbe (bark). When included in the nanoemulsion blend, the adaptogenic herbs more preferably at least include Gynostemma, American Ginseng, and Rhodiola.

Other herbs and adaptogenic compounds may be included that are chemically compatible with the PQQ, resveratrol, CoQ10, tocotrienol, and that are physically compatible with the structure of the nanoemulsion blend. While not required, the ratio of PQQ to adaptogenic herbs in water may be from 1:25 to 1:55, preferably from 1:30 to 1:50, and more preferably from 1:35 to 1:45. Thus, these ratios are based on the weight of PQQ in view of the weight of the adaptogenic herbs in water.

Phosphatidylcholine (PC) molecules are a subset of the larger set of phospholipids and are commonly used to form liposomes in water. When placed in water without other constituents, the PC forms liposomes. The application of sufficient shear forces to the PC liposomes can reduce the bilayer liposome structures to monolayer structures.

PC has a head that is water-soluble and a tail that is much less water-soluble in relation to the head. PC is a neutral lipid, but carries an electric dipole moment of about 10 D between the head and the tail, making the molecule itself polar. While "PC" is used throughout this document for convenience, PC may be substituted with or combined with other amphiphilic fats. Preferable amphiphilic fats are isolated from lecithin, and include glycerophospholipids, phosphatidylcholine, phosphatidylethanolamine, phosphatidylinositol, and phosphatidic acid.

Tocopheryl polyethylene glycol succinate 1000 (TPGS) is generally considered a surfactant having a non-polar, oil-soluble "Vitamin E" tail and a polar, water-soluble polyethylene glycol head. While some beneficial effect may be possible with regard to mitochondria protection with the TPGS directly, the oil-soluble tocotrienol forms more readily provide the desired concentration and combination of PQQ/tocotrienol within the mitochondria in relation to the other components of the nanoemulsion blend. While "TPGS" is used throughout this document for convenience, TPGS may be substituted with or combined with other polyethylene glycol surfactant forms, including polysorbate 40, 60, or 80.

The intra-oral delivery of the resveratrol provided by the PC and TPGS structures of the first monolayer surfactant-based particles of the nanoemulsion blend prevent the extensive metabolism of the resveratrol observed for conventional oral administration. A modified water-soluble form of CoQ10 could be substituted for the oil-soluble form and thus carried with the PQQ, but this is not preferred. As the oil-soluble form of CoQ10 is preferred, the PC and TPGS allows the desired ratio of CoQ10 to reach the mitochondria, which as with the resveratrol, is otherwise impossible with conventional oral delivery. Preferably, the ratio of PQQ to PC is from 1:27 to 1:43, preferably from 1:32 to 1:38, and more preferably from 1:37 to 1:43. While excess PC may be used, it is not required.

From a mitochondrial performance enhancement perspective, the PC may increase the health of or replace damaged phospholipids in the membranes forming the physical structures of the mitochondria. As efficient electron transport depends on the mitochondrial membranes having the correct physical structures, the PC is believed to enhance electron transport by improving the integrity of the mitochondrial membranes. The TPGS may provide some anti-oxidant or electron transport enhancement. However, the primary purpose of the PC and TPGS is to provide an approximately 125 nm particle average diameter and less transport system to the mitochondrial performance enhancing components that provides intra-oral component transfer to the bloodstream.

The following examples illustrate one or more preferred embodiments of the invention. Numerous variations may be made to the following examples that lie within the scope of the invention.

EXAMPLES

Example 1: Constituents of the Aqueous, Intra-Oral, Nanoemulsion Blend

A nanoemulsion blend was prepared having a 5 mL total volume. The blend included approximately 10 mg of PQQ, 15 mg of resveratrol and 30 mg of CoQ10 in associating oil, 5 mg of 70% by weight delta tocotrienol, 442 mg of PC, 400 mg of adaptogenic herb extract, approximately 500 to 1000 mg ethanol, approximately 500 to 2000 mg glycerin, and minor amounts of NaOH and flavoring. TPGS is included to provide the desired physical structures in the nanoemulsion. In addition to these ingredients, the blend included enough water to provide a total volume of 5 mL.

Example 2: A Method of Making an Aqueous, Intra-Oral, Nanoemulsion Blend Including PC Micelles Resveratrol (approximately 15 mg) was solubilized in associating oil, then combined with PC, TPGS, glycerin, and ethanol in water. The mixture was then homogenized to form an emulsion.

CoQ10 (approximately 30 mg) was in associating oil, then combined with PC, TPGS, glycerin, and ethanol in water. The mixture was then homogenized to form an emulsion.

The resveratrol and CoQ10 emulsions were mixed and tocotrienol (approximately 5 mg) was added to the mixed emulsions and mixed.

PC (approximately 400 mg) was added to glycerin and ethanol in water to form micellular PC.

The adaptogenic herb extract including water, ethanol, and glycerin (approximately 400 mg) is combined with PC, TPGS, ethanol, and acacia gum in water to form an adaptogenic herb liposome mixture.

The micellular PC and adaptogenic herb liposomes mixtures were then added to and mixed with the mixed emulsions including the tocotrienol.

PQQ (approximately 10 mg) was dissolved in warm water with NaOH and then added to the mixture.

The total volume of the mixture was then increased to approximately 5 mL with water.

The mixture was then subjected to high pressure homogenization from approximately 100 to 1000 bar to form the aqueous, intra-oral, nanoemulsion blend including PC micelles.

To provide a clear and more consistent understanding of the specification and claims of this application, the following definitions are provided.

Intra-oral delivery means that at least 50%, preferably 60%, and more preferably 80% and above of the delivery into the bloodstream that occurs upon oral administration of the liquid including the deliverable occurs by transmucosal absorption through the mouth, throat and esophagus before the liquid reaches the stomach. For particles to be considered suitable for intra-oral delivery, the average particle diameter is at most 125 nm and preferably less than 80 nm. For example, particles having an average diameter of 100 would have only an approximately 40% delivery to the bloodstream intra-orally, while particles having an average diameter of 75 nm would have and approximate 60% intra-oral delivery to the bloodstream. An 80% or greater intra-oral delivery to the bloodstream may be achieved with an average particle diameter of approximately 50 nm in 0.5 mL liquid after a mouth-residency time of 2 minutes.

Solutions lack an identifiable interface between the solubilized molecules and the solvent. In solutions, the solubilized molecules are in direct contact with the solvent.

Emulsions are mixtures of two or more liquids that do not solubilize. Thus, one of the liquids carries isolated particles in the form of droplets of the other liquid. The particles of one liquid may be said to be dispersed in the continuous phase of the other liquid. An interface, separation, or boundary layer exists between the two liquids, thus between the continuous phase and the particles. Emulsions may be macroemulsions, pseudo-emulsions, microemulsions, or nanoemulsions. The primary difference between the types of emulsions is the size (average diameter) of the particles dispersed in the continuous phase. Macroemulsions and pseudo-emulsions have average particle diameters from 1 to 20 micrometers.

Nanoemulsions have average particle diameters from 10 to 125 nanometers, thus being at least an order of magnitude smaller in average particle diameters than macro- and pseudo-emulsions.

In a continuous water phase, all the water molecules are in direct contact with other water molecules, thus providing a continuously hydrogen bonded system.

A stable dispersion may be determined in one of two ways. One way to establish that a dispersion is stable is when the oil phase particles in a continuous water phase do not change in average diameter by more than +/−20% for a time period of at least 3 months to 3 years, preferably for a time period of at least 6 months to 3 years, and more preferably, for a time period of at least 1 year to 3 years. Another way to establish that a dispersion is stable is when the oil phase particles in the continuous water phase do not separate into a visibly distinct phase with a visible meniscus for a time period of at least 6 months to 3 years, and more preferably, for a time period of at least 1 year to 3 years.

Average particle diameter is determined by dynamic light scattering (DLS), sometimes referred to a photon correlation spectroscopy. The determination is made between 20 and 25 degrees Celsius. One example of an instrument suitable for this determination is a Nicomp 380 ZLS particle sizer as available from Particle Sizing Systems, Port Richey, FL. DLS can determine the size of particles in a liquid by measuring the intensity of light scattered from the particles to a detector over time. As the particles move due to Brownian motion the light scattered from two or more particles constructively or destructively interferes at the detector. By calculating the autocorrelation function of the light intensity and assuming a particle distribution, it is possible to determine the sizes of particles from 1 nm to 5 um. The instrument is also capable of measuring the Zeta potential of particles.

PGC1-1alpha (PGC1a) is a member of a family of transcription coactivators that plays a central role in the regulation of cellular energy metabolism. PGC1a stimulates mitochondrial biogenesis and promotes the remodeling of muscle tissue to a fiber-type composition that is metabolically more oxidative and less glycolytic in nature. PGC1a also participates in the regulation of both carbohydrate and lipid metabolism. It is believed that disorders of PGC1a, such as insufficient expression, are an underlying contributor to health disorders including obesity, diabetes, and cardiomyopathy.

Endotoxins are present inside a bacterial cell and are released when the cell disintegrates. Endotoxins are sometimes responsible for the characteristic symptoms of a disease.

Heavy metals include mercury, cadmium, lead, arsenic, nickel, chromium, and antimony.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

While various aspects of the invention are described, it will be apparent to those of ordinary skill in the art that other embodiments and implementations are possible within the scope of the invention.

The invention claimed is:

1. A method of making an aqueous, intra-oral, nanoemulsion blend for enhancing mitochondrial performance in animals when orally administered, the method comprising:
   homogenizing a mixture comprising a cell-signaling pathway enhancement composition, a first portion of amphiphilic fat including at least 30% by weight phosphatidylcholine, a polyethylene glycol surfactant form, an associating oil, glycerin, ethanol, and water to form a first emulsion;
   homogenizing a mixture comprising coenzyme Q10, a second portion of amphiphilic fat including at least 30% by weight phosphatidylcholine, a polyethylene glycol surfactant form, an associating oil, glycerin, ethanol, and water to form a second emulsion;
   combining the first and second emulsions with at least one tocotrienol isomer of Vitamin E to form a third emulsion;

combining a third portion of amphiphilic fat including at least 30% by weight phosphatidylcholine with glycerin and ethanol in water to form micellular amphiphilic fat;

combining an adaptogenic herb extract including oil-and water-soluble herbs, water, ethanol, and glycerin with a fourth portion of amphiphilic fat including at least 30% by weight phosphatidylcholine, a polyethylene glycol surfactant form, additional ethanol, and acacia gum in water to form an adaptogenic herb liposome mixture;

combining the third emulsion with the micellular amphiphilic fat and the adaptogenic herb liposome mixture to form a fourth emulsion;

combining a pyrroloquinoline quinone salt dissolved in water and sodium hydroxide with the fourth emulsion to form a fifth emulsion; and homogenizing the fifth emulsion under a pressure from 100 to 1000 bar to form an aqueous, intra-oral, nanoemulsion blend including phosphatidylcholine micelles, where the blend is a shelf stable dispersion.

2. The method of claim 1, where the adaptogenic herb extract comprises Gynostemma, American Ginseng, and Rhodiola.

3. The method of claim 1, where the associating oil is selected from the group consisting essentially of medium chain triglycerides, citrus oil, and combinations thereof.

4. The method of claim 1, where the polyethylene glycol surfactant form is selected from the group consisting of tocopheryl polyethylene glycol succinate 1000, polysorbate 40, polysorbate 60, polysorbate 80, and combinations thereof.

5. The method of claim 1, where the polyethylene glycol surfactant form is tocopheryl polyethylene glycol succinate 1000.

6. The method of claim 1, where the pyrroloquinoline quinone salt is pyrroloquinoline quinone disodium salt.

7. The method of claim 6, where the ratio in the blend of the pyrroloquinoline quinone disodium salt to the coenzyme Q10 is from 1:2 to 1:4.

8. The method of claim 6, where the ratio of the pyrroloquinoline quinone disodium salt to the coenzyme Q10 is from 1:2.8 to 1:3.2.

9. The method of claim 1, where the cell signaling pathway enhancement composition is selected from the group consisting of resveratrol, genistein, and combinations thereof.

10. The method of claim 1, where the cell signaling pathway enhancement composition comprises resveratrol.

11. The method of claim 10, where the ratio in the blend of the pyrroloquinoline quinone salt to the resveratrol is from 1:1 to 1:2.

12. The method of claim 10, where the ratio in the blend of the pyrroloquinoline quinone salt to the resveratrol is from 1:1.4 to 1:1.6.

13. The method of claim 10, where the phosphatidylcholine micelles in the blend have average particle diameters from 10 nm to 125 nm.

14. The method of claim 10, where the phosphatidylcholine micelles in the blend have average particle diameters from 10 nm to 60 nm.

15. The method of claim 1, where the ratio in the blend of the pyrroloquinoline quinone salt to total amphiphilic fat including at least 30% by weight phosphatidylcholine is from 1:27 to 1:43.

16. The method of claim 1, where the ratio in the blend of the pyrroloquinoline quinone salt to total amphiphilic fat including at least 30% by weight phosphatidylcholine is from 1:37 to 1:43.

17. The method of claim 1, the blend configured to deliver at least 60% by transmucosal absorption through the mouth of a total bloodstream delivered concentration of the cell-signaling pathway enhancement composition, the coenzyme Q10, and the pyrroloquinoline quinone salt, when 0.5 mL of the blend is intra-orally administered to a human for a mouth-residency time of 2 minutes.

18. The method of claim 1, the blend configured to deliver at least 80% by transmucosal absorption through the mouth of a total bloodstream delivered concentration of the cell-signaling pathway enhancement composition, the coenzyme Q10, and the pyrroloquinoline quinone salt, when 0.5 mL of the blend is intra-orally administered to a human for a mouth-residency time of 2 minutes.

* * * * *